(12) United States Patent
Ye et al.

(10) Patent No.: US 12,296,329 B2
(45) Date of Patent: *May 13, 2025

(54) FLUIDIZED BED REGENERATOR, DEVICE FOR PREPARING LOW-CARBON OLEFINS, AND USE THEREOF

(71) Applicant: DALIAN INSTITUTE OF CHEMICAL PHYSICS, CHINESE ACADEMY OF SCIENCES, Dalian (CN)

(72) Inventors: Mao Ye, Dalian (CN); Tao Zhang, Dalian (CN); Jinling Zhang, Dalian (CN); Shuliang Xu, Dalian (CN); Hailong Tang, Dalian (CN); Xiangao Wang, Dalian (CN); Cheng Zhang, Dalian (CN); Jinming Jia, Dalian (CN); Jing Wang, Dalian (CN); Hua Li, Dalian (CN); Chenggong Li, Dalian (CN); Zhongmin Liu, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 274 days.

This patent is subject to a terminal disclaimer.

(21) Appl. No.: 17/777,052

(22) PCT Filed: Oct. 16, 2020

(86) PCT No.: PCT/CN2020/121577
§ 371 (c)(1),
(2) Date: May 16, 2022

(87) PCT Pub. No.: WO2022/077460
PCT Pub. Date: Apr. 21, 2022

(65) Prior Publication Data
US 2022/0401905 A1 Dec. 22, 2022

(51) Int. Cl.
*B01J 8/26* (2006.01)
*B01J 8/18* (2006.01)
(Continued)

(52) U.S. Cl.
CPC ............... *B01J 8/26* (2013.01); *B01J 8/1827* (2013.01); *B01J 8/1872* (2013.01); *B01J 29/85* (2013.01);
(Continued)

(58) Field of Classification Search
CPC . B01J 8/1827; B01J 8/1872; B01J 8/26; B01J 29/85; B01J 29/90; B01J 38/16;
(Continued)

(56) References Cited

U.S. PATENT DOCUMENTS

| 4,851,374 A | * | 7/1989 | Yan | .......................... | B01J 23/96 |
| | | | | | 208/120.35 |
| 2004/0186333 A1 | | 9/2004 | Lattner et al. | | |

(Continued)

FOREIGN PATENT DOCUMENTS

| CN | 102463138 A | 5/2012 |
| CN | 104419468 A | 3/2015 |

(Continued)

*Primary Examiner* — In Suk C Bullock
*Assistant Examiner* — Jason Y Chong
(74) *Attorney, Agent, or Firm* — Bayramoglu Law Offices LLC

(57) ABSTRACT

A fluidized bed regenerator, a device for preparing low-carbon olefins, and a use thereof are provided. The fluidized bed regenerator includes a second activation zone, a first activation zone, and a gas-solid separation zone from bottom to top; the second activation zone axially communicates with the gas-solid separation zone; the first activation zone is arranged on a periphery of a junction between the second activation zone and the gas-solid separation zone; the first activation zone is an annular cavity; n baffles are radially (Continued)

arranged in the first activation zone, and the n baffles divide the first activation zone into n first activation zone subzones; and a catalyst circulation hole is formed in each of n−1 of the baffles such that a catalyst entering the first activation zone flows in an annular direction.

20 Claims, 2 Drawing Sheets

(51) Int. Cl.
*B01J 29/85* (2006.01)
*B01J 29/90* (2006.01)
*B01J 38/34* (2006.01)
*C07C 1/22* (2006.01)

(52) U.S. Cl.
CPC ............... *B01J 29/90* (2013.01); *B01J 38/34* (2013.01); *C07C 1/22* (2013.01); *B01J 2208/0084* (2013.01); *B01J 2208/00991* (2013.01); *C07C 2529/85* (2013.01)

(58) Field of Classification Search
CPC ............... B01J 38/34; B01J 2208/0084; B01J 2208/00991; B01J 38/06; B01J 38/14; C07C 1/20; C07C 1/22; C07C 2529/85; C07C 11/04; C07C 11/06; Y02P 20/584; Y02P 30/20; Y02P 30/40
See application file for complete search history.

(56) References Cited

U.S. PATENT DOCUMENTS

| | | | |
|---|---|---|---|
| 2007/0203383 A1 | 8/2007 | Bozzano et al. | |
| 2016/0304413 A1* | 10/2016 | Liu | ................ B01J 29/90 |

FOREIGN PATENT DOCUMENTS

| | | |
|---|---|---|
| CN | 104672040 A | 6/2015 |
| CN | 104672044 A | 6/2015 |
| CN | 106732823 A | 5/2017 |
| CN | 107540492 A | 1/2018 |
| CN | 107961743 A | 4/2018 |
| CN | 107963957 A | 4/2018 |
| EA | 008804 B1 | 8/2007 |
| EP | 2785459 A1 | 10/2014 |
| GB | 2469195 A | 10/2010 |
| KR | 20020052184 A | 7/2002 |
| KR | 20160093676 A | 8/2016 |
| RU | 2632905 C1 | 10/2017 |
| WO | 2015081489 A1 | 6/2015 |

* cited by examiner

FLUIDIZED BED REGENERATOR, DEVICE FOR PREPARING LOW-CARBON OLEFINS, AND USE THEREOF

CROSS REFERENCE TO THE RELATED APPLICATIONS

This application is the national phase entry of International Application No. PCT/CN2020/121577, filed on Oct. 16, 2020, the entire contents of which are incorporated herein by reference.

TECHNICAL FIELD

The present application relates to a fluidized bed regenerator, a device for preparing low-carbon olefins, and use thereof, and belongs to the field of chemical catalysis.

BACKGROUND

Methanol-to-olefin technology (MTO) mainly includes DMTO (methanol-to-olefin) technology of Dalian Institute of Chemical Physics, Chinese Academy of Sciences and MTO technology of UOP Company of the United States. In 2010, the Shenhua Baotou methanol-to-olefin plant using DMTO technology was completed and put into operation. This is the world's first industrial application of MTO technology. As of the end of 2019, 14 DMTO industrial plants have been put into production, with a total production capacity of about 8 million tons of low-carbon olefins per year.

In recent years, DMTO technology has been further developed, and a new generation of DMTO catalysts with better performance have gradually begun in industrial applications, creating higher benefits for DMTO plants. The new generation of DMTO catalyst has higher methanol processing capacity and low-carbon olefin selectivity.

The MTO technologies generally adopt an SAPO-34 molecular sieve catalyst, and the high selectivity for low-carbon olefins in an MTO process is achieved by the combination of the acid catalysis of the molecular sieve with the restriction of pores in a framework structure of the molecular sieve. A methanol conversion process is also accompanied by a coking process of an acidic molecular sieve catalyst. The existing MTO plants can achieve a methanol coking rate of 1.5 wt % to 2.5 wt %, that is, 3.3% to 5.5% of carbon (C) atoms in methanol are converted into coke in the catalyst, and the coke is burned in a regenerator to generate CO, $CO_2$, $H_2O$, and the like that are discharged, with a C utilization rate only of 94.5% to 96.7%. With the advancement of technologies, the selectivity for low-carbon olefins in an MTO process has been greatly improved, but the high methanol coking rate and the low C utilization rate have become bottlenecks inhibiting the advancement of technologies. Therefore, it is necessary to develop new MTO technologies to improve the C utilization rate and the atomic economy.

SUMMARY

An MTO process is accompanied by a coking process of an acidic molecular sieve catalyst, such that coke species are formed in molecular sieve cages, triggering a catalytic process of MTO. The coking of the catalyst makes some active sites of the molecular sieve covered to reduce the activity of the catalyst, but the coke in the molecular sieve further limits pores in a framework structure of the molecular sieve to improve the selectivity for low-carbon olefins.

The low-carbon olefins mentioned in the present application refer to ethylene and propylene. The applicants have found through research that main factors affecting the activity of a DMTO catalyst and the selectivity for low-carbon olefins include coke content, coke content distribution, and coke species in the catalyst. Under the same average coke content in catalysts, the narrower the coke content distribution, the higher the selectivity and activity of low-carbon olefins. Coke species in a catalyst may include polymethyl aromatic hydrocarbons, polymethyl cycloalkanes, and the like, where polymethylbenzene and polymethylnaphthalene can promote the formation of ethylene. Therefore, the control of the coke content, coke content distribution, and coke species in a catalyst is the key to control an operation window of the DMTO catalyst and improve the selectivity of low-carbon olefins.

A coke content in an MTO spent catalyst is generally 7 wt % to 13 wt %, and a too-high coke content will greatly reduce the activity of the catalyst. At present, MTO plants generally adopt an air regeneration method to restore the activity of a catalyst, thereby recycling the catalyst; and in this process, the coke is burned in a regenerator to generate CO, $CO_2$, $H_2O$, and other substances, which are discharged. In fact, the coke in spent catalysts can be divided into two categories: coke with a large molecular weight, a high graphitization degree, and no catalytic activity, which can be called inactive coke; and polymethyl aromatic hydrocarbons and polymethyl cycloalkanes with a small molecular weight and catalytic activity, which can be called active coke. When air is used as a regeneration medium, due to the strong oxidizability of air, inactive coke and active coke undergo a deep oxidation reaction with oxygen to mainly generate substances such as CO, $CO_2$, and $H_2O$, and it is difficult to realize the controllable conversion of coke and control the coke content, coke content distribution, and coke species in the catalyst. Therefore, when air is used as a regeneration medium and a coke content in a catalyst is <3 wt %, the sufficient catalytic activity of the catalyst can be restored in the case where most coke is oxidized and eliminated. A regenerated catalyst obtained by this regeneration scheme shows low selectivity for low-carbon olefins, high methanol coking rate, and high methanol unit consumption. When water is used as a regeneration medium, active coke reacts with water, large-molecule species are converted into small-molecule species, and under suitable conditions, active coke can be converted into species mainly composed of polymethylbenzene and polymethylnaphthalene. When a combination of water and oxygen is used as a regeneration medium, under the action of oxygen and water, inactive coke and active coke are converted into oxygen-containing hydrocarbon species and oxygen-free hydrocarbon species with a small molecular weight, where oxygen-containing hydrocarbon species do not have catalytic activity. The oxygen-containing hydrocarbon species can be converted into oxygen-free hydrocarbon species with catalytic activity under the action of substances such as water vapor, hydrogen, methane, ethane, and propane.

Therefore, the present application provides a controllable activation method for converting a spent catalyst into a regenerated catalyst, where the regenerated catalyst has the characteristics of high activity, high selectivity for low-carbon olefins, and the like, and can reduce the methanol unit consumption and methanol coking rate and improve the atomic economy of the MTO technology.

According to a first aspect of the present application, a fluidized bed regenerator for activating a catalyst to prepare low-carbon olefins from an oxygen-containing compound is provided.

A fluidized bed regenerator for activating a catalyst to prepare low-carbon olefins from an oxygen-containing compound is provided, where the fluidized bed regenerator includes a second activation zone, a first activation zone, and a gas-solid separation zone from bottom to top;
- the second activation zone axially communicates with the gas-solid separation zone;
- the first activation zone is arranged on a periphery of a junction between the second activation zone and the gas-solid separation zone;
- the first activation zone is an annular cavity;
- n baffles are radially arranged in the first activation zone, and the n baffles divide the first activation zone into n first activation zone subzones; and
- a catalyst circulation hole is formed in each of n−1 of the baffles, such that a catalyst entering the first activation zone flows in an annular direction.

Optionally, in the first activation zone, the n baffles may include a $1^{st}$ baffle, and a $2^{nd}$ baffle to an $n^{th}$ baffle;
- no catalyst circulation hole is formed in the $1^{st}$ baffle;
- a catalyst circulation hole is formed in each of the $2^{nd}$ baffle to the $n^{th}$ baffle;
- a spent catalyst inlet is formed in a $1^{st}$ first activation zone subzone formed through division by the 1st baffle and the $2^{nd}$ baffle;
- a first activation zone catalyst delivery pipe is arranged in an $n^{th}$ first activation zone subzone formed through division by the $1^{st}$ baffle and the $n^{th}$ baffle;
- a first activation zone distributor is arranged beneath the first activation zone subzones; and
- a first activation zone gas delivery pipe is arranged at tops of the first activation zone subzones.

Specifically, one or more catalyst circulation holes can be formed in each of the baffles, which is not strictly limited in the present application. When a plurality of catalyst circulation holes are formed, relative positions of the catalyst circulation holes are not strictly limited in the present application. For example, the plurality of catalyst circulation holes may be arranged in parallel, or may be arranged randomly.

Preferably, a first activation zone distributor may be provided beneath each of the first activation zone subzones. In this way, a first activation zone raw material can enter the first activation zone subzones uniformly as a whole.

Preferably, a top of each of the first activation zone subzones may be provided with a first activation zone gas delivery pipe.

Specifically, the first activation zone raw material may contact and react with a spent catalyst through the first activation zone distributor.

Optionally, a first gas-solid separation unit of the regenerator may be arranged in an upper part of the first activation zone; and
the first gas-solid separation unit of the regenerator may communicate with the first activation zone through the spent catalyst inlet.

Specifically, the spent catalyst may enter the first activation zone through the first gas-solid separation unit.

Specifically, the first activation zone may be provided with a first activation zone catalyst delivery pipe, an inlet of the first activation zone catalyst delivery pipe may be connected to the $n^{th}$ first activation zone subzone, and an outlet of the first activation zone catalyst delivery pipe may be formed in the second activation zone.

Optionally, the first gas-solid separation unit of the regenerator may be a gas-solid cyclone separator.

Optionally, n may have a value range of $2 \leq n \leq 10$.

Optionally, a cross section of each of the first activation zone subzones may be sector-annular.

Optionally, m perforated plates may be horizontally arranged in the second activation zone, where $1 \leq m \leq 10$.

Optionally, the perforated plates may have a porosity of 5% to 50%.

In the present application, perforated plates are arranged in the second activation zone to inhibit the back-mixing of a catalyst among beds and improve the uniformity of coke distribution in the catalyst.

Optionally, a second activation zone distributor may be arranged at a bottom of the second activation zone.

Optionally, the fluidized bed regenerator may include a regenerator gas collection chamber and a fluidized bed regenerator cooler;
- the regenerator gas collection chamber may be located at a top of the fluidized bed regenerator;
- a top of the regenerator gas collection chamber may be provided with a regenerator product gas delivery pipe;
- the gas-solid separation zone may be provided with a second gas-solid separation unit;
- the regenerator gas collection chamber may be connected to an outlet of the second gas-solid separation unit; and
- the fluidized bed regenerator cooler may be located in a lower part of the second activation zone.

Specifically, an inner diameter of a junction between the second activation zone and the gas-solid separation zone may gradually increase.

Specifically, an inner diameter of a junction between the lower shell and the upper shell of the fluidized bed regenerator may gradually increase.

Optionally, the second gas-solid separation unit of the regenerator may adopt one or more sets of gas-solid cyclone separators.

Preferably, each set of gas-solid cyclone separators may include a first-stage gas-solid cyclone separator and a second-stage gas-solid cyclone separator.

As a preferred embodiment, the fluidized bed regenerator may be divided into a second activation zone, a first activation zone, and a gas-solid separation zone from bottom to top;
- the fluidized bed regenerator may include a regenerator shell, a first gas-solid separation unit of the regenerator, a first activation zone distributor, a baffle, a first activation zone catalyst delivery pipe, a first activation zone gas delivery pipe, a second activation zone distributor, a perforated plate, a fluidized bed regenerator cooler, a second gas-solid separation unit of the regenerator, a regenerator gas collection chamber, a regenerator product gas delivery pipe, a regenerated catalyst inclined pipe, a regenerated catalyst slide valve, and a regenerated catalyst delivery pipe;
- the first activation zone may be located in an annular zone above the second activation zone, n baffles may be arranged in the first activation zone, and the baffles may divide the first activation zone into n first activation zone subzones, where $2 \leq n \leq 10$; a bottom of each of the first activation zone subzones may be independently provided with a first activation zone distributor; a cross section of the first activation zone may be annular, and a cross section of each of the first activation zone subzones may be sector-annular; the $1^{st}$ to $n^{th}$ first activation zone subzones may be concentrically arranged in sequence; a catalyst circulation hole may be formed in the baffles, but no catalyst circulation hole may be formed in a baffle between the $1^{st}$ first activation zone subzone and the $n^{th}$ first activation zone subzone;

the first gas-solid separation unit of the regenerator may be located in the gas-solid separation zone of the fluidized bed regenerator; an inlet of the first gas-solid separation unit of the regenerator may be connected to an outlet of the spent catalyst delivery pipe, a gas outlet of the first gas-solid separation unit of the regenerator may be formed in the gas-solid separation zone, and a catalyst outlet of the first gas-solid separation unit of the regenerator may be formed in the $1^{st}$ first activation zone subzone;

an inlet of the first activation zone catalyst delivery pipe may be connected to the $n^{th}$ first activation zone subzone, and an outlet of the first activation zone catalyst delivery pipe may be formed in the second activation zone; a top of each of the first activation zone subzones may be independently provided with a first activation zone gas delivery pipe, and an outlet of the first activation zone gas delivery pipe may be formed in the gas-solid separation zone;

the second activation zone distributor may be located at a bottom of the second activation zone of the fluidized bed regenerator, and m perforated plates may be arranged in the second activation zone, where 1≤m≤10; the fluidized bed regenerator cooler may be located in the second activation zone;

the second gas-solid separation unit of the regenerator and the regenerator gas collection chamber may be located in the gas-solid separation zone of the fluidized bed regenerator; an inlet of the second gas-solid separation unit of the regenerator may be formed in the gas-solid separation zone of the fluidized bed regenerator, a gas outlet of the second gas-solid separation unit of the regenerator may be connected to the regenerator gas collection chamber, and a catalyst outlet of the second gas-solid separation unit of the regenerator may be formed in the second activation zone; the regenerator product gas delivery pipe may be connected to a top of the regenerator gas collection chamber;

an inlet of the regenerated catalyst inclined pipe may be connected to a lower part of the second activation zone; and an inlet of the regenerated catalyst slide valve may be connected to an outlet of the regenerated catalyst inclined pipe, an outlet of the regenerated catalyst slide valve may be connected to an inlet of the regenerated catalyst delivery pipe through a pipeline, and an outlet of the regenerated catalyst delivery pipe may be connected to the reaction zone of the fluidized bed reactor.

According to a second aspect of the present application, a device for preparing low-carbon olefins from an oxygen-containing compound is provided. The device is a DMTO device including a fluidized bed reactor and a fluidized bed regenerator.

A device for preparing low-carbon olefins from an oxygen-containing compound is provided, including a fluidized bed reactor and the fluidized bed regenerator described above.

Optionally, the device may include a spent catalyst inclined pipe, a fluidized bed reactor stripper, a spent catalyst delivery pipe, a regenerated catalyst inclined pipe, and a regenerated catalyst delivery pipe;

a spent catalyst zone, the spent catalyst inclined pipe, the fluidized bed reactor stripper, the spent catalyst delivery pipe, and the first gas-solid separation unit of the regenerator may communicate with each other in sequence; and the second activation zone, the regenerated catalyst inclined pipe, the regenerated catalyst delivery pipe, and a reaction zone of the fluidized bed reactor may communicate with each other in sequence.

Specifically, the spent catalyst inclined pipe, the fluidized bed reactor stripper, and the spent catalyst delivery pipe may be connected to each other in sequence;

the regenerated catalyst inclined pipe and the regenerated catalyst delivery pipe may be connected to each other in sequence;

an inlet of the regenerated catalyst inclined pipe may be connected to a lower part of the second activation zone;

a spent catalyst undergoing a reaction in the fluidized bed reactor may enter the spent catalyst inclined pipe, and then enter the fluidized bed regenerator through the spent catalyst delivery pipe; and a regenerated catalyst obtained from the fluidized bed regenerator may enter the regenerated catalyst inclined pipe, and then enter the fluidized bed reactor through the regenerated catalyst delivery pipe.

Optionally, the fluidized bed reactor stripper and the spent catalyst delivery pipe may be connected to each other through a spent catalyst slide valve.

Optionally, the regenerated catalyst inclined pipe and the regenerated catalyst delivery pipe may be connected to each other through a regenerated catalyst slide valve.

Optionally, the fluidized bed reactor may include a lower shell, a delivery pipe, and an upper shell;

the lower shell may enclose a reaction zone;

the delivery pipe may be located above the reaction zone and may communicate with the reaction zone;

the upper shell may be arranged on a periphery of the delivery pipe;

the upper shell and the delivery pipe may enclose a cavity; and the cavity may be divided into a spent catalyst zone and a gas-solid separation zone from bottom to top.

Specifically, an inner diameter of a junction between the reaction zone of the fluidized bed reactor and the delivery pipe may gradually decrease.

Specifically, an inner diameter of a junction between the lower shell and the upper shell of the fluidized bed reactor may gradually increase.

Optionally, the reaction zone may be a fast fluidized zone.

Optionally, the spent catalyst zone may be a bubbling fluidized zone.

In the present application, a fluidization type of the reaction zone is not strictly limited, and preferably the reaction zone may be a fast fluidized zone. In the reaction zone, an apparent gas linear velocity can reach 7.0 m/s, a methanol flux is high, a methanol treatment capacity per unit volume of the device is large, and a methanol weight hourly space velocity (WHSV) can reach 20 $h^{-1}$. In the present application, a fluidization type of the spent catalyst zone is not strictly limited, and preferably the spent catalyst zone may be a bubbling fluidized zone. The spent catalyst zone may be configured to reduce a temperature of a spent catalyst, convey a low-temperature spent catalyst to the reaction zone, increase a bed density of the reaction zone, and control a bed temperature of the reaction zone. When the apparent gas linear velocity is 0.5 m/s to 7.0 m/s, a corresponding bed density is 500 kg/m³ to 100 kg/m³.

Optionally, the gas-solid separation zone may be provided with a first gas-solid separation unit of the fluidized bed reactor; and an upper part of the delivery pipe may be connected to an inlet of the first gas-solid separation unit of the fluidized bed reactor.

Optionally, the fluidized bed reactor may include a fluidized bed reactor distributor, a fluidized bed reactor cooler, a spent catalyst zone gas distributor, a fluidized bed reactor gas collection chamber, and a second gas-solid separation unit of the fluidized bed reactor;

the fluidized bed reactor distributor may be located at a bottom of the reaction zone;

the fluidized bed reactor cooler may be located in a lower part of the spent catalyst zone;

the spent catalyst zone gas distributor may be located in a lower part of the spent catalyst zone;

gas outlets of the second gas-solid separation unit of the fluidized bed reactor and the first gas-solid separation unit of the fluidized bed reactor may be connected to the fluidized bed reactor gas collection chamber;

the fluidized bed reactor gas collection chamber may be provided with a product gas delivery pipe; and catalyst outlets of the first gas-solid separation unit of the fluidized bed reactor and the second gas-solid separation unit of the fluidized bed reactor may be connected to the spent catalyst zone.

Specifically, a raw material with an oxygen-containing compound may contact and react with a regenerated catalyst through the fluidized bed reactor distributor.

Specifically, the spent catalyst zone fluidizing gas may contact a spent catalyst through the spent catalyst zone gas distributor.

Optionally, the reaction zone and the spent catalyst zone may communicate with each other through a spent catalyst circulation pipe.

Specifically, an inlet of the spent catalyst circulation pipe may be connected to the spent catalyst zone; and an outlet of the spent catalyst circulation pipe may be connected to a bottom of the reaction zone.

Optionally, the spent catalyst circulation pipe may be provided with a spent catalyst circulation slide valve.

Optionally, the first gas-solid separation unit of the fluidized bed reactor may adopt one or more sets of gas-solid cyclone separators.

Preferably, each set of gas-solid cyclone separators may include a first-stage gas-solid cyclone separator and a second-stage gas-solid cyclone separator.

Optionally, the second gas-solid separation unit of the fluidized bed reactor may adopt one or more sets of gas-solid cyclone separators.

Preferably, each set of gas-solid cyclone separators may include a first-stage gas-solid cyclone separator and a second-stage gas-solid cyclone separator.

As a preferred embodiment, the fluidized bed reactor may include a fluidized bed reactor shell, a fluidized bed reactor distributor, a delivery pipe, a first gas-solid separation unit of the fluidized bed reactor, a fluidized bed reactor gas collection chamber, a spent catalyst zone gas distributor, a fluidized bed reactor cooler, a second gas-solid separation unit of the fluidized bed reactor, a product gas delivery pipe, a spent catalyst circulation pipe, a spent catalyst circulation slide valve, a spent catalyst inclined pipe, a fluidized bed reactor stripper, a spent catalyst slide valve, and a spent catalyst delivery pipe;

a lower part of the fluidized bed reactor may be a reaction zone, a middle part thereof may be a spent catalyst zone, and an upper part thereof may be a gas-solid separation zone;

the fluidized bed reactor distributor may be located at a bottom of the reaction zone of the fluidized bed reactor, the delivery pipe may be located in central zones of the middle and upper parts of the fluidized bed reactor, and a bottom end of the delivery pipe may be connected to a top end of the reaction zone; an upper part of the delivery pipe may be connected to an inlet of the first gas-solid separation unit of the fluidized bed reactor, and the first gas-solid separation unit of the fluidized bed reactor may be located in the gas-solid separation zone of the fluidized bed reactor; a gas outlet of the first gas-solid separation unit of the fluidized bed reactor may be connected to the fluidized bed reactor gas collection chamber, and a catalyst outlet of the first gas-solid separation unit of the fluidized bed reactor may be formed in the spent catalyst zone; a spent catalyst zone gas distributor may be located at a bottom of the spent catalyst zone, and the fluidized bed reactor cooler may be located in the spent catalyst zone; the second gas-solid separation unit of the fluidized bed reactor may be located in the gas-solid separation zone of the fluidized bed reactor, an inlet of the second gas-solid separation unit of the fluidized bed reactor may be formed in the gas-solid separation zone of the fluidized bed reactor, a gas outlet of the second gas-solid separation unit of the fluidized bed reactor may be connected to the fluidized bed reactor gas collection chamber, and a catalyst outlet of the second gas-solid separation unit of the fluidized bed reactor may be formed in the spent catalyst zone; the fluidized bed reactor gas collection chamber may be located at a top of the fluidized bed reactor, and the product gas delivery pipe may be connected to a top of the fluidized bed reactor gas collection chamber; an inlet of the spent catalyst circulation pipe may be connected to the spent catalyst zone, and an outlet of the spent catalyst circulation pipe may be connected to a bottom of the reaction zone of the fluidized bed reactor; a spent catalyst circulation slide valve may be arranged in the spent catalyst circulation pipe, an inlet of the spent catalyst inclined pipe may be connected to the spent catalyst zone, and an outlet of the spent catalyst inclined pipe may be connected to an upper part of the fluidized bed reactor stripper; the fluidized bed reactor stripper may be arranged outside the fluidized bed reactor shell; and an inlet of the spent catalyst slide valve may be connected to a bottom of the fluidized bed reactor stripper through a pipeline, an outlet of the spent catalyst slide valve may be connected to an inlet of the spent catalyst delivery pipe through a pipeline, and an outlet of the spent catalyst delivery pipe may be connected to the fluidized bed regenerator.

According to a third aspect of the present application, a method for activating a catalyst to prepare low-carbon olefins from an oxygen-containing compound is provided.

A method for activating a catalyst to prepare low-carbon olefins from an oxygen-containing compound is provided, which adopts the fluidized bed regenerator described above.

Optionally, the method may include:

feeding a first activation zone raw material and a spent catalyst into the first activation zone, where the spent catalyst chemically reacts with the first activation zone raw material while flowing in an annular direction along the first activation zone subzones to generate a partially-activated catalyst; and feeding the partially-activated catalyst and a second activation zone raw material into the second activation zone, and allowing a chemical reaction to generate a regenerated catalyst;

where a coke composition in the partially-activated catalyst includes oxygen-containing hydrocarbon species and oxygen-free hydrocarbon species.

Optionally, the first activation zone raw material may enter the first activation zone through the first activation zone distributor to react with coke in the catalyst.

Optionally, the second activation zone raw material may enter the second activation zone through the second activation zone distributor to react with coke in the catalyst.

Specifically, while the spent catalyst flows in an annular direction along catalyst circulation holes formed in the baffles, the first activation zone raw material enters the first activation zone subzone from the first activation zone distributor located beneath, and contacts the spent catalyst, such that inactive coke and active coke in the spent catalyst are converted into oxygen-containing hydrocarbon species and oxygen-free hydrocarbon species with a small molecular weight; and a gas phase (including the unreacted first activation zone raw material) is conveyed to the gas-solid separation zone through the first activation zone gas delivery pipe above the first activation zone.

Specifically, the catalyst enters the second activation zone through the first activation zone catalyst delivery pipe, and the second activation zone raw material enters the second activation zone through the second activation zone distributor located beneath to contact the catalyst, such that catalytically-inactive oxygen-containing hydrocarbon species in coke of the catalyst are converted into catalytically-active oxygen-free hydrocarbon species; and a gas phase (including the unreacted second activation zone raw material) enters the gas-solid separation zone.

Optionally, the coke in the spent catalyst may chemically react with the first activation zone raw material to generate a first activation zone product gas.

Optionally, the coke in the partially-activated catalyst may chemically react with the second activation zone raw material to generate a second activation zone product gas.

Optionally, the first activation zone product gas and the second activation zone product gas may be mixed in the gas-solid separation zone to produce a regenerator product gas.

Optionally, a regenerator product gas carrying a catalyst may enter the second gas-solid separation unit of the regenerator to undergo gas-solid separation to obtain a regenerator product gas and a catalyst;

the regenerator product gas may enter the regenerator gas collection chamber; and the catalyst may be returned to the second activation zone of the fluidized bed regenerator.

Optionally, the regenerator product gas may include CO, $H_2$, and $CO_2$; and a content of the CO and the $H_2$ may be greater than 90 wt %.

Optionally, the first activation zone raw material may include oxygen, air, and water vapor;

a mass fraction of the oxygen may be 0 wt % to 10 wt %;
a mass fraction of the air may be 0 wt % to 20 wt %; and
a mass fraction of the water vapor is 80 wt % to 100 wt %.

Optionally, the second activation zone raw material may be water vapor.

Optionally, a coke content in the spent catalyst may be 9 wt % to 13 wt %.

Preferably, a coke content in the spent catalyst may be 10 wt % to 12 wt %.

Optionally, a coke content in the regenerated catalyst may be 5 wt % to 11 wt %; and a quartile deviation of a coke content distribution in the regenerated catalyst may be less than 1.0 wt %.

Optionally, in the regenerated catalyst, coke species may include polymethylbenzene and polymethylnaphthalene;

a total mass of the polymethylbenzene and the polymethylnaphthalene may account for greater than or equal to 60 wt % of a total mass of coke;

a mass of coke species with a molecular weight greater than 184 may account for less than or equal to 30 wt % of the total mass of coke; and the total mass of coke may refer to a total mass of coke species.

In the present application, types and contents of coke species are very important; and the coke content and coke content distribution in a catalyst are controlled by controlling an average residence time and a residence time distribution of the catalyst in the first activation zone and the second activation zone to make a proportion of a mass of polymethylbenzene and polymethylnaphthalene in a total mass of coke greater than or equal to 60 wt %, which improves the activity of the catalyst and the selectivity for low-carbon olefins.

Optionally, the spent catalyst may include an SAPO-34 molecular sieve.

In the present application, an active component in the catalyst may be an SAPO-34 molecular sieve.

Optionally, process operating conditions of the first activation zone of the fluidized bed regenerator may be as follows: apparent gas linear velocity: 0.1 m/s to 0.5 m/s; temperature: 650° C. to 750° C.; pressure: 100 kPa to 500 kPa; and bed density: 400 kg/m³ to 700 kg/m³.

Optionally, process operating conditions of the second activation zone of the fluidized bed regenerator may be as follows: apparent gas linear velocity: 0.1 m/s to 0.5 m/s; temperature: 550° C. to 700° C.; pressure: 100 kPa to 500 kPa; and bed density: 400 kg/m³ to 700 kg/m³.

The first activation zone of the fluidized bed regenerator in the present application includes n first activation zone subzones, and a catalyst can only flow from an upstream subzone to a downstream subzone in order through the catalyst circulation holes on the baffles in the first activation zone, which shows the following beneficial effects: 1. Process operating conditions can be changed to control an average residence time of a catalyst in the first activation zone, thereby controlling a coke content in the catalyst. 2. The structure of n first activation zone subzones is adopted to control a residence time distribution of a catalyst (the residence time distribution is similar to n serially-connected completely-mixed tank reactors), and thus a regenerated catalyst with a narrow coke content distribution can be obtained.

In the present application, since the catalyst is powdery, the coke content in the catalyst refers to an average coke content in catalyst granules, but coke contents in different catalyst granules may actually be different. In the present application, the quartile deviation of the coke content distribution in the regenerated catalyst can be controlled to be less than 1.0 wt %, such that the overall coke content distribution of the catalyst is narrow, thereby improving the activity of the catalyst and the selectivity for low-carbon olefins.

In the fluidized bed regenerator of the present application, an activation process of a catalyst includes two steps: S1. water vapor and oxygen are used as an activation gas to convert the inactive coke and active coke in the spent catalyst into oxygen-containing hydrocarbons species and oxygen-free hydrocarbon species with a small molecular weight, where the oxygen-containing hydrocarbon species show no catalytic activity and S1 is completed in the first activation zone; and S2. water vapor is used as an activation gas to convert the catalytically-inactive oxygen-containing hydrocarbon species in the coke into catalytically-active oxygen-free hydrocarbon species and further reduce the molecular weight of coke, that is, the coke in the catalyst is converted into species mainly composed of polymethylbenzene and polymethylnaphthalene, where S2 is completed in the second activation zone. In S1, the activation gas used can decompose the inactive coke due to strong oxidizability, but leads to the generation of some catalytically-inactive oxygen-containing hydrocarbon species; and in S2, a non-oxidative activation gas is used to further convert the catalytically-inactive oxygen-containing hydrocarbon species into catalytically-active oxygen-free hydrocarbon species. After the two-step activation, coke species in the regenerated catalyst are mainly polymethylbenzene and polymethylnaphthalene, with high selectivity for ethylene.

In the fluidized bed regenerator in the present application, a regeneration process of a catalyst is the coupling of an exothermic reaction and an endothermic reaction, where the first activation zone raw material and the coke in the catalyst react in the first activation zone to generate substances such as CO and $H_2$, and the release of heat raises a temperature of the bed; and the second activation zone raw material and the coke in the catalyst react in the second activation zone to generate substances such as CO and $H_2$, this reaction is an endothermic reaction, and the heat required by the reaction is supplied by the exothermic reaction in the first activation zone.

As a preferred embodiment, a first activation zone raw material may be fed into the first activation zone of the fluidized bed regenerator from the first activation zone distributor; a spent catalyst may be fed into the first gas-solid separation unit of the regenerator from the spent catalyst delivery pipe to undergo gas-solid separation, a resulting gas may be discharged into the gas-solid separation zone of the fluidized bed regenerator through the gas outlet of the first gas-solid separation unit of the regenerator, and a resulting spent catalyst may be discharged into the first activation zone of the fluidized bed regenerator through the catalyst outlet of the first gas-solid separation unit of the regenerator; the first activation zone raw material may contact and chemically react with the spent catalyst in the first activation zone, such that the inactive coke and active coke in the spent catalyst are converted into oxygen-containing hydrocarbon species and oxygen-free hydrocarbon species with a small molecular weight and a first activation zone product gas is generated; a catalyst in the first activation zone may pass through the $1^{st}$ to $n^{th}$ first activation zone subzones in sequence through catalyst circulation holes on the baffles and then enter the second activation zone of the fluidized bed regenerator through the first activation zone catalyst delivery pipe; the first activation zone product gas may enter the gas-solid separation zone of the fluidized bed regenerator through the first activation zone gas delivery pipe; a second activation zone raw material may be fed into the second activation zone of the fluidized bed regenerator from the second activation zone distributor to contact and chemically react with a catalyst from the first activation zone, such that catalytically-inactive oxygen-containing hydrocarbon species in the coke are converted into catalytically-active oxygen-free hydrocarbon species, a molecular weight of the coke is further reduced (that is, the coke in the catalyst is converted into species mainly composed of polymethylbenzene and polymethylnaphthalene; and a catalyst discharged from the second activation zone is called a regenerated catalyst), and the second activation zone raw material is converted into a second activation zone product gas in the second activation zone and then enters the gas-solid separation zone of the fluidized bed regenerator; the first activation zone product gas and the second activation zone product gas may be mixed in the gas-solid separation zone to produce a regenerator product gas, and the regenerator product gas may carry a catalyst and enter the second gas-solid separation unit of the regenerator to undergo gas-solid separation to obtain a regenerator product gas and a catalyst; the regenerator product gas may enter the regenerator gas collection chamber and then enter a downstream regenerator product gas recycling system through the regenerator product gas delivery pipe, and the catalyst may be returned to the second activation zone of the fluidized bed regenerator; the regenerated catalyst in the second activation zone may be cooled, and then enter the fluidized bed reactor through the regenerated catalyst inclined pipe, the regenerated catalyst slide valve, and the regenerated catalyst delivery pipe.

In the present application, the main components in the regenerator product gas are CO, $H_2$, and a small amount of $CO_2$, where a total content of CO and $H_2$ is greater than 90 wt % and a content of $CO_2$ is less than 10 wt % (dry basis, excluding the unconverted $H_2O$); after the regenerator product gas is subjected to simple separation, a mixed gas of CO and $H_2$ can be obtained, and the mixed gas of CO and $H_2$ can be recycled as a raw material for methanol preparation; and thus, in the technical solution of the present application, the coke generated from methanol is an intermediate product of this process, and the utilization rate of C atoms in the whole process is greater than or equal to 99%.

According to a fourth aspect of the present application, a method for preparing low-carbon olefins from an oxygen-containing compound is provided.

A method for preparing low-carbon olefins from an oxygen-containing compound is provided, which adopts the device described above.

Optionally, the method may include:
feeding a raw material with the oxygen-containing compound and a regenerated catalyst into the reaction zone, and allowing a reaction to obtain a stream A with low-carbon olefins and a spent catalyst;
subjecting the stream A to gas-solid separation, and conveying the spent catalyst to the spent catalyst zone; and
returning a part of the spent catalyst in the spent catalyst zone to a fluidized bed reaction zone, and allowing the remaining part of the spent catalyst to enter the fluidized bed regenerator.

Specifically, a part of the spent catalyst in the spent catalyst zone is returned to the fluidized bed reaction zone through the spent catalyst circulation pipe, and the remaining part of the spent catalyst enters the fluidized bed regenerator through the spent catalyst inclined pipe, the fluidized bed reactor stripper, and the spent catalyst delivery pipe.

Optionally, the regenerated catalyst regenerated from the spent catalyst by the fluidized bed regenerator may enter the reaction zone of the fluidized bed reactor through the regenerated catalyst delivery pipe.

Optionally, while the regenerated catalyst enters the reaction zone of the fluidized bed reactor, a raw material with an oxygen-containing compound may be fed into the reaction zone of the fluidized bed reactor through the fluidized bed reactor distributor to allow a reaction to obtain a stream A with low-carbon olefins and a spent catalyst.

Optionally, the stream A with low-carbon olefins and a spent catalyst may enter the first gas-solid separation unit of the fluidized bed reactor through the delivery pipe to undergo gas-solid separation to obtain a low-carbon olefin-containing gas and a spent catalyst.

Optionally, the low-carbon olefin-containing gas may enter the fluidized bed reactor gas collection chamber.

Optionally, the spent catalyst may be stripped and then enter the fluidized bed regenerator.

Optionally, the spent catalyst zone fluidizing gas may be at least one from the group consisting of nitrogen and water vapor.

Optionally, the raw material with an oxygen-containing compound may be at least one from the group consisting of methanol and dimethyl ether (DME).

Optionally, a ratio of a mass flow rate of the regenerated catalyst to a feed amount of the oxygen-containing compound (catalyst-to-alcohol ratio) may be 0.3 to 1.0 ton of catalyst/ton of methanol.

Preferably, the catalyst-to-alcohol ratio may be 0.5 to 1.0 ton of catalyst/ton of methanol.

Optionally, process operating conditions of the reaction zone of the fluidized bed reactor may be as follows: apparent gas linear velocity: 0.5 m/s to 7.0 m/s; reaction temperature: 350° C. to 550° C.; reaction pressure: 100 kPa to 500 kPa; and bed density: 100 kg/m$^3$ to 500 kg/m$^3$.

Optionally, process operating conditions of the spent catalyst zone of the fluidized bed reactor may be as follows: apparent gas linear velocity: 0.1 m/s to 1.0 m/s; reaction temperature: 350° C. to 550° C.; reaction pressure: 100 kPa to 500 kPa; and bed density: 200 kg/m$^3$ to 800 kg/m$^3$.

Optionally, the raw material with an oxygen-containing compound may react with the regenerated catalyst in the reaction zone of the fluidized bed reactor to obtain a stream A with low-carbon olefins and a spent catalyst, and the stream A may enter the first gas-solid separation unit of the fluidized bed reactor through a delivery pipe to undergo gas-solid separation to obtain a gas-phase stream B and a solid-phase stream C; the solid-phase stream C may enter the spent catalyst zone, and the spent catalyst zone fluidizing gas and the solid-phase stream C may form a stream D; and the stream D may enter the second gas-solid separation unit of the fluidized bed reactor to undergo gas-solid separation to obtain a gas-phase stream E and a solid-phase stream F; the solid-phase stream F may be returned to the spent catalyst zone, and the spent catalyst in the spent catalyst zone may be stripped and then enter the fluidized bed regenerator; and the regenerated catalyst regenerated by the fluidized bed regenerator may enter the reaction zone of the fluidized bed reactor through the regenerated catalyst delivery pipe.

Optionally, a part of the spent catalyst in the spent catalyst zone may be returned to a bottom of the reaction zone of the fluidized bed reactor through a spent catalyst circulation pipe.

Optionally, the solid-phase stream C and the solid-phase stream F may each include a spent catalyst.

Optionally, the gas-phase stream B and the gas-phase stream E may be mixed in the fluidized bed reactor gas collection chamber to produce a product gas; and the gas-phase stream B may include low-carbon olefins.

In the present application, the reaction zone is a fast fluidized zone, which can achieve an apparent gas linear velocity of 7.0 m/s, a relatively high methanol flux, a large methanol treatment capacity per unit volume of the device, and a methanol WHSV of 20 h$^{-1}$; and the spent catalyst zone is a bubbling fluidized zone, which is configured to reduce a temperature of a spent catalyst, convey a low-temperature spent catalyst to the reaction zone, increase a bed density of the reaction zone, and control a bed temperature of the reaction zone. When the apparent gas linear velocity is 0.5 m/s to 7.0 m/s, a corresponding bed density is 500 kg/m$^3$ to 100 kg/m$^3$.

In the present application, the structure in which the first gas-solid separation unit of the fluidized bed reactor is directly connected to the delivery pipe realizes the rapid separation of a low-carbon olefin-containing gas and a spent catalyst in the stream A, and avoids that low-carbon olefins further react under the action of the spent catalyst to generate hydrocarbon by-products with a large molecular weight.

As a preferred embodiment, a raw material with an oxygen-containing compound may be fed into the reaction zone of the fluidized bed reactor from the fluidized bed reactor distributor and contact a regenerated catalyst from the regenerated catalyst delivery pipe to generate a stream A with low-carbon olefins and a spent catalyst; the stream A may enter the first gas-solid separation unit of the fluidized bed reactor through the delivery pipe to undergo gas-solid separation to obtain a gas-phase stream B and a solid-phase stream C, where the gas-phase stream B is a gas with low-carbon olefins and the solid-phase stream C is a spent catalyst; the gas-phase stream B may enter the fluidized bed reactor gas collection chamber, and the solid-phase stream C may enter the spent catalyst zone; a spent catalyst zone fluidizing gas may be fed into the spent catalyst zone from the spent catalyst zone gas distributor and contact the spent catalyst, and the spent catalyst zone fluidizing gas and a spent catalyst carried thereby may form a stream D; the stream D may enter the second gas-solid separation unit of the fluidized bed reactor to undergo gas-solid separation to obtain a gas-phase stream E and a solid-phase stream F, where the gas-phase stream E is the spent catalyst zone fluidizing gas and the solid-phase stream F is the spent catalyst; the gas-phase stream E may enter the fluidized bed reactor gas collection chamber, and the solid-phase stream F may be returned to the spent catalyst zone; the gas-phase stream B and the gas-phase stream E may be mixed in the fluidized bed reactor gas collection chamber to produce a product gas, and the product gas may enter a downstream working section through the product gas delivery pipe; a part of the spent catalyst in the spent catalyst zone may be returned to a bottom of the reaction zone of the fluidized bed reactor through the spent catalyst circulation pipe and the spent catalyst circulation slide valve, and the remaining part of the spent catalyst may enter the fluidized bed reactor stripper through the spent catalyst inclined pipe to undergo stripping, and then enter the fluidized bed regenerator through the spent catalyst slide valve and the spent catalyst delivery pipe; and a regenerated catalyst regenerated by the fluidized bed regenerator may enter the fluidized bed reactor through the regenerated catalyst inclined pipe, the regenerated catalyst slide valve, and the regenerated catalyst delivery pipe.

In the present application, the "catalyst-to-alcohol ratio" refers to a ratio of a mass flow rate of the regenerated catalyst to a feed amount of the oxygen-containing compound. When a catalyst-to-alcohol ratio is expressed in the present application, a mass of DME in the oxygen-containing compound is equivalently converted into a mass of methanol according to a mass of the element C.

In the method of the present application, the product gas may be composed of 38 wt % to 55 wt % of ethylene, 37 wt % to 54 wt % of propylene, less than or equal to 6 wt % of $C_4$-$C_6$ hydrocarbon compounds, and less than or equal to 3 wt % of other components; and the other components may be methane, ethane, propane, hydrogen, CO, $CO_2$, and the like, and the total selectivity of ethylene and propylene in the product gas may be 92 wt % to 97 wt %.

In the present application, when the unit consumption of production is expressed, a mass of DME in the oxygen-containing compound is equivalently converted into a mass of methanol based on a mass of the element C, and a unit of the unit consumption of production is ton of methanol/ton of low-carbon olefins.

In the method of the present application, the unit consumption of production may be 2.4 to 2.5 tons of methanol/ton of low-carbon olefins.

Possible beneficial effects of the present application:
(1) The coke species in the regenerated catalyst are mainly polymethylbenzene and polymethylnaphthalene, with high selectivity for ethylene.
(2) The coke content and coke content distribution in a catalyst are controlled by controlling an average residence time and a residence time distribution of the catalyst in the first activation zone and the second activation zone.
(3) The perforated plates are adopted to inhibit the back-mixing of a catalyst among beds and improve the uniformity of coke distribution in the catalyst.
(4) The coke in the spent catalyst is converted into CO and $H_2$ while the spent catalyst is activated; the CO and $H_2$ can be recycled as a raw material for methanol preparation, that is, the coke generated from methanol is an intermediate product of this process; and a utilization rate of C atoms in the whole process is greater than or equal to 99%.

REFERENCE NUMERALS IN FIG. 1 AND FIG. 2

1 represents a fluidized bed reactor; 1-1 represents a fluidized bed reactor shell; 1-2 represents a fluidized bed reactor distributor; 1-3 represents a delivery pipe; 1-4 represents a first gas-solid separation unit of the fluidized bed reactor; 1-5 represents a fluidized bed reactor gas collection chamber; 1-6 represents a spent catalyst zone gas distributor; 1-7 represents a fluidized bed reactor cooler; 1-8 represents a second gas-solid separation unit of the fluidized bed reactor; 1-9 represents a product gas delivery pipe; 1-10 represents a spent catalyst circulation pipe; 1-11 represents a spent catalyst circulation slide valve; 1-12 represents a spent catalyst inclined pipe; 1-13 represents a fluidized bed reactor stripper; 1-14 represents a spent catalyst slide valve; 1-15 represents a spent catalyst delivery pipe;

2 represents a fluidized bed regenerator; 2-1 represents a regenerator shell; 2-2 represents a first gas-solid separation unit of the regenerator; 2-3 represents a first activation zone distributor; 2-4 represents a baffle; 2-5 represents a first activation zone catalyst delivery pipe; 2-6 represents a first activation zone gas delivery pipe; 2-7 represents a second activation zone distributor; 2-8 represents a perforated plate; 2-9 represents a fluidized bed regenerator cooler; 2-10 represents a second gas-solid separation unit of the regenerator; 2-11 represents a regenerator gas collection chamber; 2-12 represents a regenerator product gas delivery pipe; 2-13 represents a regenerated catalyst inclined pipe; 2-14 represents a regenerated catalyst slide valve; and 2-15 represents a regenerated catalyst delivery pipe.

DETAILED DESCRIPTION OF THE EMBODIMENTS

The present application will be described in detail below with reference to examples, but the present application is not limited to these examples.

Unless otherwise specified, the raw materials and catalysts in the examples of the present application are all purchased from commercial sources.

Figure 1:
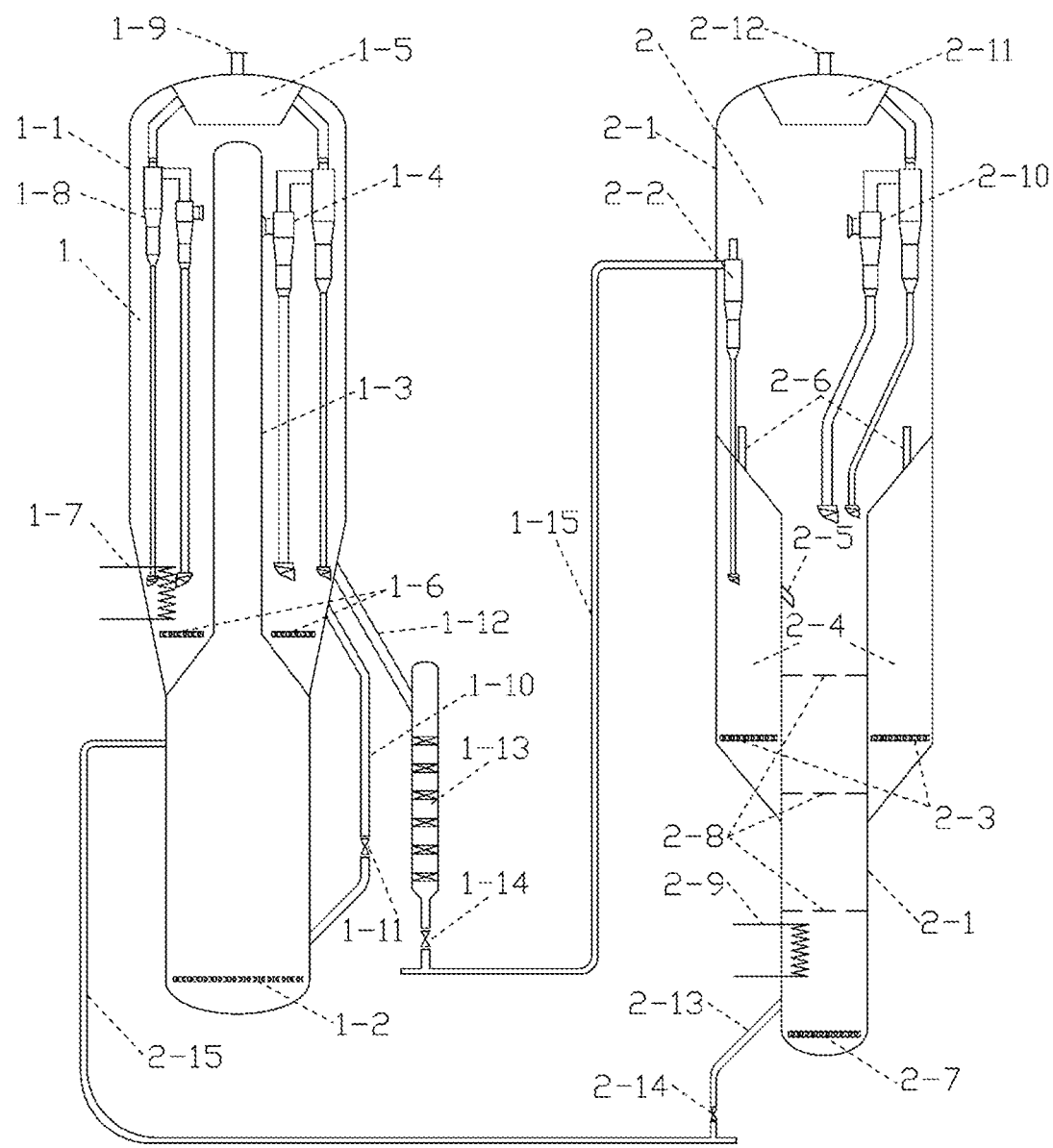
FIG. 1 is a schematic diagram of a DMTO device for preparing low-carbon olefins from an oxygen-containing compound according to an embodiment of the present application.
Figure 2:
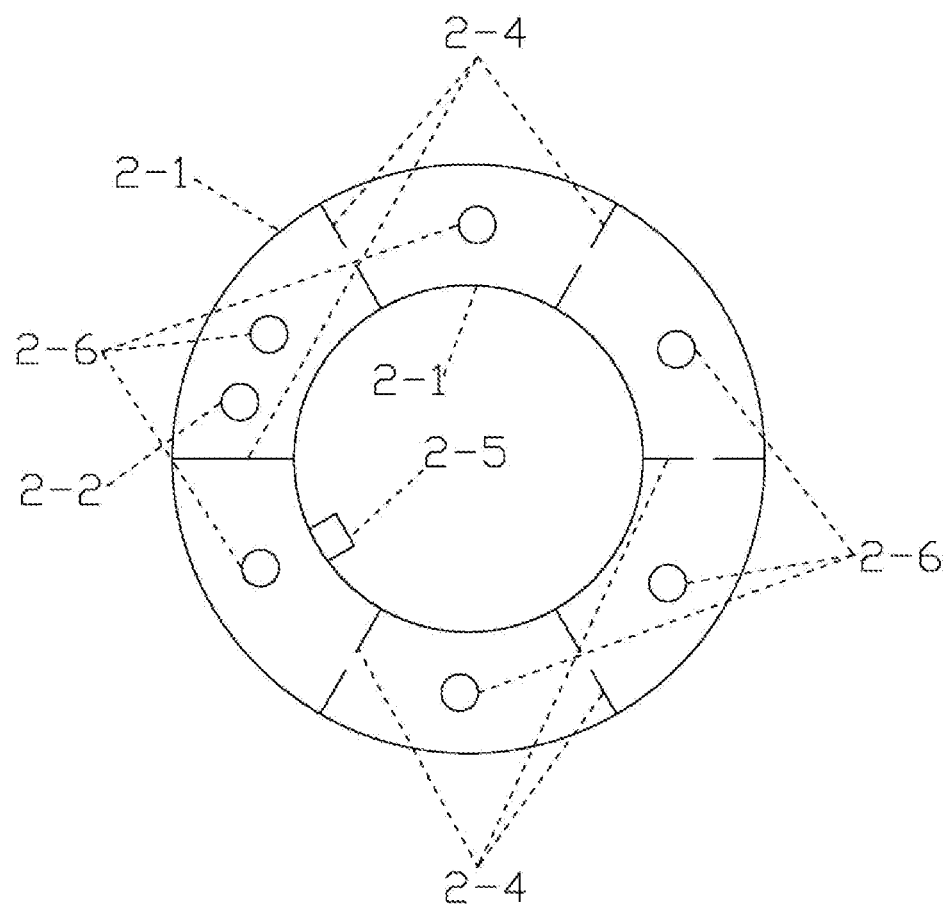
FIG. 2 is a schematic diagram of a cross section of the first activation zone in FIG. 1.

As an embodiment of the present application, a schematic diagram of a DMTO device is shown in FIG. 1 and FIG. 2, and the device includes a fluidized bed reactor (1) and a fluidized bed regenerator (2). Specifically:

As shown in FIG. 1, the fluidized bed reactor (1) includes a fluidized bed reactor shell (1-1), a fluidized bed reactor distributor (1-2), a delivery pipe (1-3), a first gas-solid separation unit (1-4) of the fluidized bed reactor, a fluidized bed reactor gas collection chamber (1-5), a spent catalyst zone gas distributor (1-6), a fluidized bed reactor cooler (1-7), a second gas-solid separation unit (1-8) of the fluidized bed reactor, a product gas delivery pipe (1-9), a spent catalyst circulation pipe (1-10), a spent catalyst circulation slide valve (1-11), a spent catalyst inclined pipe (1-12), a fluidized bed reactor stripper (1-13), a spent catalyst slide valve (1-14), and a spent catalyst delivery pipe (1-15); a lower part of the fluidized bed reactor (1) is a reaction zone, a middle part thereof is a spent catalyst zone, and an upper part thereof is a gas-solid separation zone; the fluidized bed reactor distributor (1-2) is located at a bottom of the reaction zone of the fluidized bed reactor (1), the delivery pipe (1-3) is located in central zones of the middle and upper parts of the fluidized bed reactor (1), and a bottom end of the delivery pipe (1-3) is connected to a top end of the reaction zone; an upper part of the delivery pipe (1-3) is connected to an inlet of the first gas-solid separation unit (1-4) of the fluidized bed reactor, and the first gas-solid separation unit (1-4) of the fluidized bed reactor is located in the gas-solid separation zone of the fluidized bed reactor (1); a gas outlet of the first gas-solid separation unit (1-4) of the fluidized bed reactor is connected to the fluidized bed reactor gas collection chamber (1-5), and a catalyst outlet of the first gas-solid separation unit (1-4) of the fluidized bed reactor is formed in the spent catalyst zone; a spent catalyst zone gas distributor (1-6) is located at a bottom of the spent catalyst zone, and the fluidized bed reactor cooler (1-7) is located in the spent catalyst zone; the second gas-solid separation unit (1-8) of the fluidized bed reactor is located in the gas-solid separation zone of the fluidized bed reactor (1), an inlet of the second gas-solid separation unit (1-8) of the fluidized bed reactor is formed in the gas-solid separation zone of the fluidized bed reactor (1), a gas outlet of the second gas-solid separation unit (1-8) of the fluidized bed reactor is connected to the fluidized bed reactor gas collection chamber (1-5), and a catalyst outlet of the second gas-solid separation unit (1-8) of the fluidized bed reactor is formed in the spent catalyst zone; the fluidized bed reactor gas collection chamber (1-5) is located at a top of the fluidized bed reactor (1), and the product gas delivery pipe (1-9) is connected to a top of the fluidized bed reactor gas collection chamber (1-5); an inlet of the spent catalyst circulation pipe (1-10) is connected to the spent catalyst zone, and an outlet of the spent catalyst circulation pipe (1-10) is connected to a bottom of the reaction zone of the fluidized bed reactor (1); a spent catalyst circulation slide valve (1-11) is arranged in the spent catalyst circulation pipe (1-10), an inlet of the spent catalyst inclined pipe (1-12) is connected to the spent catalyst zone, and an outlet of the spent catalyst inclined pipe (1-12) is connected to an upper part of the fluidized bed reactor stripper (1-13); the fluidized bed reactor stripper (1-13) is arranged outside the fluidized bed reactor shell (1-1); an inlet of the spent catalyst slide valve (1-14) is connected to a bottom of the fluidized bed reactor stripper (1-13) through a pipeline, and an outlet of the spent catalyst slide valve (1-14) is connected to an inlet of the spent catalyst delivery pipe (1-15) through a pipeline; and an outlet of the spent catalyst delivery pipe (1-15) is connected to the fluidized bed regenerator (2). The first gas-solid separation unit (1-4) of the fluidized bed reactor may adopt multiple sets of gas-solid cyclone separators, and each of the multiple sets of gas-solid cyclone separators may include a first-stage gas-solid cyclone separator and a second-stage gas-solid cyclone separator; and the second gas-solid separation unit (1-8) of the fluidized bed reactor may adopt multiple sets of gas-solid cyclone separators, and each of the multiple sets of gas-solid cyclone separators may include a first-stage gas-solid cyclone separator and a second-stage gas-solid cyclone separator.

As shown in FIG. 1, the fluidized bed regenerator (2) includes a regenerator shell (2-1), a first gas-solid separation unit (2-2) of the regenerator, a first activation zone distributor (2-3), a baffle (2-4), a first activation zone catalyst delivery pipe (2-5), a first activation zone gas delivery pipe (2-6), a second activation zone distributor (2-7), a perforated plate (2-8), a fluidized bed regenerator cooler (2-9), a second gas-solid separation unit (2-10) of the regenerator, a regenerator gas collection chamber (2-11), a regenerator product gas delivery pipe (2-12), a regenerated catalyst inclined pipe (2-13), a regenerated catalyst slide valve (2-14), and a regenerated catalyst delivery pipe (2-15); the fluidized bed regenerator (2) is divided into a second activation zone, a first activation zone, and a gas-solid separation zone from bottom to top; the first activation zone is located in an annular zone above the second activation zone, n baffles (2-4) are arranged in the first activation zone, and the baffles (2-4) divide the first activation zone into n first activation zone subzones; a bottom of each of the first activation zone subzones is independently provided with a first activation zone distributor (2-3); a cross section of the first activation zone is annular, and a cross section of each of the first activation zone subzones is sector-annular; the $1^{st}$ to $n^{th}$ first activation zone subzones are concentrically arranged in sequence; a catalyst circulation hole is formed in the baffles (2-4), and no catalyst circulation hole is formed in a baffle between the $1^{st}$ first activation zone subzone and the $n^{th}$ first activation zone subzone; the first gas-solid separation unit (2-2) of the regenerator is located in the gas-solid separation zone of the fluidized bed regenerator (2); an inlet of the first gas-solid separation unit (2-2) of the regenerator is connected to an outlet of the spent catalyst delivery pipe (1-15), a gas outlet of the first gas-solid separation unit (2-2) of the regenerator is formed in the gas-solid separation zone, and a catalyst outlet of the first gas-solid separation unit (2-2) of the regenerator is formed in the $1^{st}$ first activation zone subzone; an inlet of the first activation zone catalyst delivery pipe (2-5) is connected to the $n^{th}$ first activation zone subzone, and an outlet of the first activation zone catalyst delivery pipe (2-5) is formed in the second activation zone; a top of each of the first activation zone subzones is independently provided with a first activation zone gas delivery pipe (2-6), and an outlet of the first activation zone gas delivery pipe (2-6) is formed in the gas-solid separation zone; a second activation zone distributor (2-7) is located at a bottom of the second activation zone of the fluidized bed regenerator (2), m perforated plates (2-8) are arranged in the second activation zone, and a fluidized bed regenerator cooler (2-9) is located in the second activation zone; the second gas-solid separation unit (2-10) of the regenerator and the regenerator gas collection chamber (2-11) are located in the gas-solid separation zone of the fluidized bed regenerator (2); an inlet of the second gas-solid separation unit (2-10) of the regenerator is formed in the gas-solid separation zone of the fluidized bed regenerator (2), a gas outlet of the second gas-solid separation unit (2-10) of the regenerator is connected to the regenerator gas collection chamber (2-11), and a catalyst outlet of the second gas-solid separation unit (2-10) of the regenerator is formed in the second activation zone; the regenerator product gas delivery pipe (2-12) is connected to a top of the regenerator gas collection chamber (2-11); an inlet of the regenerated catalyst inclined pipe (2-13) is connected to a lower part of the second activation zone, an inlet of the regenerated catalyst slide valve (2-14) is connected to an outlet of the regenerated catalyst inclined pipe (2-13), and an outlet of the regenerated catalyst slide valve (2-14) is connected to an inlet of the regenerated catalyst delivery pipe (2-15) through a pipeline; an outlet of the regenerated catalyst delivery pipe (2-15) is connected to the reaction zone of the fluidized bed reactor (1); the second gas-solid separation unit (2-10) of the regenerator adopts multiple sets of gas-solid cyclone separators; and each of the multiple sets of gas-solid cyclone separators includes a first-stage gas-solid cyclone separator and a second-stage gas-solid cyclone separator.

As a specific embodiment of the present application, the method for preparing low-carbon olefins from an oxygen-containing compound in the present application includes:

a raw material with an oxygen-containing compound is fed into the reaction zone of the fluidized bed reactor (1) from the fluidized bed reactor distributor (1-2) and contacts a regenerated catalyst from the regenerated catalyst delivery pipe (2-15) to generate a stream A with low-carbon olefins and a spent catalyst; the stream A enters the first gas-solid separation unit (1-4) of the fluidized bed reactor through the delivery pipe (1-3) to undergo gas-solid separation to obtain a gas-phase stream B and a solid-phase stream C, where the gas-phase stream B is a gas with low-carbon olefins and the solid-phase stream C is a spent catalyst; the gas-phase stream B enters the fluidized bed reactor gas collection chamber (1-5), and the solid-phase stream C enters the spent catalyst zone; a spent catalyst zone fluidizing gas is fed into the spent catalyst zone from the spent catalyst zone gas distributor (1-6) and contacts the spent catalyst, and the spent catalyst zone fluidizing gas and a spent catalyst carried thereby form a stream D; the stream D enters the second gas-solid separation unit (1-8) of the fluidized bed reactor to undergo gas-solid separation to obtain a gas-phase stream E and a solid-phase stream F, where the gas-phase stream E is the spent catalyst zone fluidizing gas and the solid-phase stream F is the spent catalyst; the gas-phase stream E enters the fluidized bed reactor gas collection chamber (1-5), and the solid-phase stream F is returned to the spent catalyst zone; the gas-phase stream B and the gas-phase stream E are mixed in the fluidized bed reactor gas collection chamber (1-5) to produce a product gas, and the product gas enters a downstream working section through the product gas delivery pipe (1-9); a part of the spent catalyst in the spent catalyst zone is returned to a bottom of the reaction zone of the fluidized bed reactor (1) through the spent catalyst circulation pipe (1-10) and the spent catalyst circulation slide valve (1-11), and the remaining part of the spent catalyst enters the fluidized bed reactor stripper (1-13) through the spent catalyst inclined pipe (1-12) to undergo stripping, and then enters the fluidized bed regenerator (2) through the spent catalyst slide valve (1-14) and the spent catalyst delivery pipe (1-15);

a first activation zone raw material is fed into the first activation zone of the fluidized bed regenerator (2) from the first activation zone distributor (2-3); a spent catalyst is fed into the first gas-solid separation unit (2-2) of the regenerator from the spent catalyst delivery pipe (1-15) to undergo gas-solid separation, a resulting gas is discharged into the gas-solid separation zone of the fluidized bed regenerator (2) through the gas outlet of the first gas-solid separation unit (2-2) of the regenerator, and a resulting spent catalyst is discharged into the first activation zone of the fluidized bed regenerator (2) through the catalyst outlet of the first gas-solid separation unit (2-2) of the regenerator; the first activation zone raw material contacts and chemically reacts with the spent catalyst in the first activation zone, such that the inactive coke and active coke in the spent catalyst are converted into oxygen-containing hydrocarbon species and oxygen-free hydrocarbon species with a small molecular weight and a first activation zone product gas is generated; a catalyst in the first activation zone passes through the $1^{st}$ to $n^{th}$ first activation zone subzones in sequence through catalyst circulation holes on the baffles (2-4) and then enters the second activation zone of the fluidized bed regenerator (2) through the first activation zone catalyst delivery pipe (2-5); the first activation zone product gas enters the gas-solid separation zone of the fluidized bed regenerator (2) through the first activation zone gas delivery pipe (2-6); a second activation zone raw material is fed into the second activation zone of the fluidized bed regenerator (2) from the second activation zone distributor (2-7) to contact and chemically react with a catalyst from the first activation zone, such that catalytically-inactive oxygen-containing hydrocarbon species in the coke are converted into catalytically-active oxygen-free hydrocarbon species, a molecular weight of the coke is further reduced (that is, the coke in the catalyst is converted into species mainly composed of polymethylbenzene and polymethylnaphthalene; and a catalyst discharged from the second activation zone is called a regenerated catalyst), and the second activation zone raw material is converted into a second activation zone product gas in the second activation zone and then enters the gas-solid separation zone of the fluidized bed regenerator (2); the first activation zone product gas and the second activation zone product gas are mixed in the gas-solid separation zone to produce a regenerator product gas, and the regenerator product gas carries a catalyst and enters the second gas-solid separation unit (2-10) of the regenerator to undergo gas-solid separation to obtain a regenerator product gas and a catalyst; the regenerator product gas enters the regenerator gas collection chamber (2-11) and then enters a downstream regenerator product gas recycling system through the regenerator product gas delivery pipe (2-12), and the catalyst is returned to the second activation zone of the fluidized bed regenerator (2); the regenerated catalyst in the second activation zone is cooled, and then enters the fluidized bed reactor (1) through the regenerated catalyst inclined pipe (2-13), the regenerated catalyst slide valve (2-14), and the regenerated catalyst delivery pipe (2-15).

In order to well illustrate the present application and facilitate the understanding of the technical solutions of the present application, typical but non-limiting examples of the present application are as follows:

Example 1

The device shown in FIG. 1 and FIG. 2 is adopted in this example, where the first gas-solid separation unit (2-2) of the regenerator is a gas-solid cyclone separator; 2 baffles (2-4) are arranged in the first activation zone of the fluidized bed regenerator (2), that is, n=2; the baffles (2-4) divide the first activation zone into 2 first activation zone subzones; and 10 perforated plates (2-8) are arranged in the second activation zone of the fluidized bed regenerator (2), that is, m=10; and the perforated plates (2-8) have a porosity of 50%.

In this example, the oxygen-containing compound is methanol; the spent catalyst zone fluidizing gas is nitrogen; the first activation zone raw material includes 10 wt % of oxygen and 90 wt % of water vapor; the second activation zone raw material is water vapor; an active component in the catalyst is an SAPO-34 molecular sieve; a coke content in the regenerated catalyst is about 5 wt %, where coke species include polymethylbenzene and polymethylnaphthalene, a mass of polymethylbenzene and polymethylnaphthalene accounts for about 72 wt % of a total mass of coke, a mass of coke species with a molecular weight greater than 184 accounts for about 19 wt % of a total mass of coke, and a quartile deviation of coke content distribution in the regenerated catalyst is about 0.9 wt %; a coke content in the spent catalyst is about 9 wt %; the reaction zone of the fluidized bed reactor (1) is a fast fluidized zone, and process operating conditions of the reaction zone of the fluidized bed reactor (1) are as follows: apparent gas linear velocity: about 7.0 m/s, reaction temperature: about 550° C., reaction pressure: about 100 kPa, and bed density: about 100 kg/m$^3$; process operating conditions of the spent catalyst zone of the fluidized bed reactor (1) are as follows: apparent gas linear velocity: about 1.0 m/s, reaction temperature: about 550° C., reaction pressure: about 100 kPa, and bed density: about 200 kg/m$^3$; process operating conditions of the first activation zone of the fluidized bed regenerator (2) are as follows: apparent gas linear velocity: 0.5 m/s, temperature: 750° C., pressure: 100 kPa, and bed density: 400 kg/m$^3$; and process operating conditions of the second activation zone of the fluidized bed regenerator (2) are as follows: apparent gas linear velocity: 0.5 m/s, temperature: 700° C., pressure: 100 kPa, and bed density: 400 kg/m$^3$.

In this example, the catalyst-to-alcohol ratio is about 0.3 ton of catalyst/ton of methanol; the product gas is composed of 55 wt % of ethylene, 37 wt % of propylene, 5 wt % of $C_4$-$C_6$ hydrocarbon compounds, and 3 wt % of other components, where the other components include methane, ethane, propane, hydrogen, CO, $CO_2$, and the like; and the unit consumption of production is 2.50 tons of methanol/ton of low-carbon olefins. The utilization rate of C atoms in the whole process is 99.0%.

Example 2

The device shown in FIG. 1 and FIG. 2 is adopted in this example, where the first gas-solid separation unit (2-2) of the regenerator is a gas-solid cyclone separator; 10 baffles (2-4) are arranged in the first activation zone of the fluidized bed regenerator (2), that is, n=10; the baffles (2-4) divide the first activation zone into 10 first activation zone subzones; and 1 perforated plate (2-8) is arranged in the second activation zone of the fluidized bed regenerator (2), that is, m=1; and the perforated plate (2-8) has a porosity of 5%.

In this example, the oxygen-containing compound includes 82 wt % of methanol and 18 wt % of DME; the spent catalyst zone fluidizing gas is water vapor; the first activation zone raw material includes 20 wt % of air and 80 wt % of water vapor; the second activation zone raw material is water vapor; an active component in the catalyst is an SAPO-34 molecular sieve; a coke content in the regenerated catalyst is about 7 wt %, where coke species include polymethylbenzene and polymethylnaphthalene, a mass of polymethylbenzene and polymethylnaphthalene accounts for about 66 wt % of a total mass of coke, a mass of coke species with a molecular weight greater than 184 accounts for about 26 wt % of a total mass of coke, and a quartile deviation of coke content distribution in the regenerated catalyst is about 0.6 wt %; a coke content in the spent catalyst is about 11 wt %; process operating conditions of the reaction zone of the fluidized bed reactor (1) are as follows: apparent gas linear velocity: about 0.5 m/s, reaction temperature: about 350° C., reaction pressure: about 500 kPa, and bed density: about 500 kg/m$^3$; the spent catalyst zone of fluidized bed reactor (1) is a bubbling fluidized zone, and process operating conditions of the spent catalyst zone of the fluidized bed reactor (1) are as follows: apparent gas linear velocity: about 0.1 m/s, reaction temperature: about 350° C., reaction pressure: about 500 kPa, and bed density: about 800 kg/m$^3$; process operating conditions of the first activation zone of the fluidized bed regenerator (2) are as follows: apparent gas linear velocity: 0.3 m/s, temperature: 700° C., pressure: 500 kPa, and bed density: 510 kg/m$^3$; and process operating conditions of the second activation zone of the fluidized bed regenerator (2) are as follows: apparent gas linear velocity: 0.3 m/s, temperature: 550° C., pressure: 500 kPa, and bed density: 510 kg/m$^3$.

In this example, the catalyst-to-alcohol ratio is about 0.5 ton of catalyst/ton of methanol; the product gas is composed of 38 wt % of ethylene, 54 wt % of propylene, 6 wt % of $C_4$-$C_6$ hydrocarbon compounds, and 2 wt % of other components, where the other components include methane, ethane, propane, hydrogen, CO, $CO_2$, and the like; and the unit consumption of production is 2.50 tons of methanol/ton of low-carbon olefins. The utilization rate of C atoms in the whole process is 99.3%.

Example 3

The device shown in FIG. 1 and FIG. 2 is adopted in this example, where the first gas-solid separation unit (2-2) of the regenerator is a gas-solid rapid separator; 4 baffles (2-4) are arranged in the first activation zone of the fluidized bed regenerator (2), that is, n=4; the baffles (2-4) divide the first activation zone into 4 first activation zone subzones; and 6 perforated plates (2-8) are arranged in the second activation zone of the fluidized bed regenerator (2), that is, m=6; and the perforated plate (2-8) has a porosity of 30%.

In this example, the oxygen-containing compound is DME; the spent catalyst zone fluidizing gas includes 5 wt % of nitrogen and 95 wt % of water vapor; the first activation zone raw material includes 1 wt % of oxygen and 99 wt % of water vapor; the second activation zone raw material is water vapor; an active component in the catalyst is an SAPO-34 molecular sieve; a coke content in the regenerated catalyst is about 9 wt %, where coke species include polymethylbenzene and polymethylnaphthalene, a mass of polymethylbenzene and polymethylnaphthalene accounts for about 79 wt % of a total mass of coke, a mass of coke species with a molecular weight greater than 184 accounts for about 13 wt % of a total mass of coke, and a quartile deviation of coke content distribution in the regenerated catalyst is about 0.2 wt %; a coke content in the spent catalyst is about 12 wt %; process operating conditions of the reaction zone of the fluidized bed reactor (1) are as follows: apparent gas linear velocity: about 3.0 m/s, reaction temperature: about 450° C., reaction pressure: about 300 kPa, and bed density: about 230 kg/m$^3$; process operating conditions of the spent catalyst zone of the fluidized bed reactor (1) are as follows: apparent gas linear velocity: about 0.2 m/s, reaction temperature: about 450° C., reaction pressure: about 300 kPa, and bed density: about 600 kg/m$^3$; process operating conditions of the first activation zone of the fluidized bed regenerator (2) are as follows: apparent gas linear velocity: 0.2 m/s, temperature: 680° C., pressure: 300 kPa, and bed density: 580 kg/m$^3$; and process operating conditions of the second activation zone of the fluidized bed regenerator (2) are as follows: apparent gas linear velocity: 0.2 m/s, temperature: 630° C., pressure: 300 kPa, and bed density: 580 kg/m$^3$.

In this example, the catalyst-to-alcohol ratio is about 0.8 ton of catalyst/ton of methanol; the product gas is composed of 45 wt % of ethylene, 51 wt % of propylene, 3 wt % of $C_4$-$C_6$ hydrocarbon compounds, and 1 wt % of other components, where the other components include methane, ethane, propane, hydrogen, CO, $CO_2$, and the like; and the unit consumption of production is 2.42 tons of methanol/ton of low-carbon olefins. The utilization rate of C atoms in the whole process is 99.5%.

Example 4

The device shown in FIG. 1 and FIG. 2 is adopted in this example, where the first gas-solid separation unit (2-2) of the regenerator is a gas-solid rapid separator; 8 baffles (2-4) are arranged in the first activation zone of the fluidized bed regenerator (2), that is, n=8; the baffles (2-4) divide the first activation zone into 8 first activation zone subzones; and 4 perforated plates (2-8) are arranged in the second activation zone of the fluidized bed regenerator (2), that is, m=4; and the perforated plate (2-8) has a porosity of 20%.

In this example, the oxygen-containing compound is methanol; the spent catalyst zone fluidizing gas is water vapor; the first activation zone raw material includes 5 wt % of air and 95 wt % of water vapor; the second activation zone raw material is water vapor; an active component in the catalyst is an SAPO-34 molecular sieve; a coke content in the regenerated catalyst is about 11 wt %, where coke species include polymethylbenzene and polymethylnaphthalene, a mass of polymethylbenzene and polymethylnaphthalene accounts for about 88 wt % of a total mass of coke, a mass of coke species with a molecular weight greater than 184 accounts for about 7 wt % of a total mass of coke, and a quartile deviation of coke content distribution in the regenerated catalyst is about 0.1 wt %; a coke content in the spent catalyst is about 13 wt %; process operating conditions of the reaction zone of the fluidized bed reactor (1) are as follows: apparent gas linear velocity: about 4.0 m/s, reaction temperature: about 500° C., reaction pressure: about 200 kPa, and bed density: about 160 kg/m$^3$; process operating conditions of the spent catalyst zone of the fluidized bed reactor (1) are as follows: apparent gas linear velocity: about 0.5 m/s, reaction temperature: about 500° C., reaction pressure: about 200 kPa, and bed density: about 300 kg/m$^3$; process operating conditions of the first activation zone of the fluidized bed regenerator (2) are as follows: apparent gas linear velocity: 0.1 m/s, temperature: 650° C., pressure: 200 kPa, and bed density: 700 kg/m$^3$; and process operating conditions of the second activation zone of the fluidized bed regenerator (2) are as follows: apparent gas linear velocity: 0.1 m/s, temperature: 600° C., pressure: 200 kPa, and bed density: 700 kg/m$^3$.

In this example, the catalyst-to-alcohol ratio is about 1.0 ton of catalyst/ton of methanol; the product gas is composed of 51 wt % of ethylene, 46 wt % of propylene, 2 wt % of $C_4$-$C_6$ hydrocarbon compounds, and 1 wt % of other components, where the other components include methane, ethane, propane, hydrogen, CO, $CO_2$, and the like; and the unit consumption of production is 2.40 tons of methanol/ton of low-carbon olefins. The utilization rate of C atoms in the whole process is 99.6%.

The above examples are merely few examples of the present application, and do not limit the present application in any form. Although the present application is disclosed as above with preferred examples, the present application is not limited thereto. Some changes or modifications made by any technical personnel familiar with the profession using the technical content disclosed above without departing from the scope of the technical solutions of the present application are equivalent to equivalent implementation cases and fall within the scope of the technical solutions.

What is claimed is:

1. A fluidized bed regenerator for activating a catalyst to prepare low-carbon olefins from an oxygen-containing compound, wherein the fluidized bed regenerator comprises a second activation zone, a first activation zone, and a gas-solid separation zone from bottom to top;
   the second activation zone axially communicates with the gas-solid separation zone;
   the first activation zone is arranged on a periphery of a junction between the second activation zone and the gas-solid separation zone;
   the first activation zone is an annular cavity;
   n baffles are radially arranged in the first activation zone, and the n baffles divide the first activation zone into n first activation zone subzones; and
   a catalyst circulation hole is formed in each of n−1 of the baffles, and a catalyst entering the first activation zone flows in an annular direction.

2. The fluidized bed regenerator according to claim 1, wherein in the first activation zone, the n baffles comprise a $1^{st}$ baffle, and a $2^{nd}$ baffle to an $n^{th}$ baffle;
   no catalyst circulation hole is formed in the $1^{st}$ baffle;
   a catalyst circulation hole is formed in each of the $2^{nd}$ baffle to the $n^{th}$ baffle;
   a spent catalyst inlet is formed in a $1^{st}$ first activation zone subzone formed through division by the $1^{st}$ baffle and the $2^{nd}$ baffle;
   a first activation zone catalyst delivery pipe is arranged in an $n^{th}$ first activation zone subzone formed through division by the $1^{st}$ baffle and the $n^{th}$ baffle;
   a first activation zone distributor is arranged beneath the first activation zone subzones;
   a first activation zone gas delivery pipe is arranged at tops of the first activation zone subzones;
   n has a value range of 2≤n≤10; and
   a cross section of each of the first activation zone subzones is sector-annular.

3. The fluidized bed regenerator according to claim 2, wherein a gas-solid separation unit of the regenerator is arranged in the gas-solid separation zone; and
   the gas-solid separation unit of the regenerator communicates with the first activation zone through the spent catalyst inlet.

4. A device for preparing low-carbon olefins from an oxygen-containing compound, comprising a fluidized bed reactor and the fluidized bed regenerator of claim 3.

5. The device according to claim 4, wherein the device comprises a spent catalyst inclined pipe, a fluidized bed reactor stripper, a spent catalyst delivery pipe, a regenerated catalyst inclined pipe, and a regenerated catalyst delivery pipe;
   a spent catalyst zone, the spent catalyst inclined pipe, the fluidized bed reactor stripper, the spent catalyst delivery pipe, and the gas-solid separation unit of the regenerator communicate with each other in sequence; and
   the second activation zone, the regenerated catalyst inclined pipe, the regenerated catalyst delivery pipe, and a reaction zone of the fluidized bed reactor communicate with each other in sequence.

6. The device according to claim 5, wherein the fluidized bed reactor comprises a lower shell, a delivery pipe, and an upper shell;
   the lower shell encloses the reaction zone;
   the delivery pipe is located above the reaction zone and communicates with the reaction zone;
   the upper shell is arranged on a periphery of the delivery pipe;
   the upper shell and the delivery pipe enclose a cavity;
   the cavity is divided into a spent catalyst zone and a gas-solid separation zone from bottom to top;
   the reaction zone is a fast fluidized zone;
   the spent catalyst zone is a bubbling fluidized zone;
   the gas-solid separation zone is provided with a first gas-solid separation unit of the fluidized bed reactor;
   an upper part of the delivery pipe is connected to an inlet of the first gas-solid separation unit of the fluidized bed reactor;
   the fluidized bed reactor comprises a fluidized bed reactor distributor, a fluidized bed reactor cooler, a spent catalyst zone gas distributor, a fluidized bed reactor gas collection chamber, and a gas-solid separation unit of the fluidized bed reactor;
   the fluidized bed reactor distributor is located at a bottom of the reaction zone;
   the fluidized bed reactor cooler is located in a lower part of the spent catalyst zone;
   the spent catalyst zone gas distributor is located in the lower part of the spent catalyst zone;
   gas outlets of the gas-solid separation unit of the fluidized bed reactor and the first gas-solid separation unit of the fluidized bed reactor are connected to the fluidized bed reactor gas collection chamber;
   the fluidized bed reactor gas collection chamber is provided with a product gas delivery pipe;
   catalyst outlets of the first gas-solid separation unit of the fluidized bed reactor and the gas-solid separation unit of the fluidized bed reactor are connected to the spent catalyst zone; and
   the reaction zone and the spent catalyst zone communicate with each other through a spent catalyst circulation pipe.

7. A method for preparing low-carbon olefins from an oxygen-containing compound using the device according to claim 6, comprising:
activating a catalyst to prepare the low-carbon olefins from the oxygen-containing compound using the fluidized bed regenerator; wherein
a method activating the catalyst to prepare the low-carbon olefins from the oxygen-containing compound comprises:
feeding a first activation zone raw material and a spent catalyst into the first activation zone, wherein the spent catalyst chemically reacts with the first activation zone raw material while flowing in an annular direction along the first activation zone subzones to generate a partially-activated catalyst; and
feeding the partially-activated catalyst and a second activation zone raw material into the second activation zone, and allowing a chemical reaction to generate a regenerated catalyst;
wherein a coke composition in the partially-activated catalyst comprises oxygen-containing hydrocarbon species and oxygen-free hydrocarbon species;
the method for preparing the low-carbon olefins from the oxygen-containing compound further comprises:
feeding a raw material with the oxygen-containing compound and the regenerated catalyst into the reaction zone, and allowing a reaction to obtain a first stream with the low-carbon olefins and the spent catalyst;
subjecting the first stream to gas-solid separation, and conveying the spent catalyst to the spent catalyst zone; and
returning a part of the spent catalyst in the spent catalyst zone to a fluidized bed reaction zone, and allowing the remaining part of the spent catalyst to enter the fluidized bed regenerator.

8. The method according to claim 7, a fluidizing gas of the spent catalyst zone is at least one from the group consisting of nitrogen and water vapor.

9. The method according to claim 7, wherein the raw material with the oxygen-containing compound is at least one from the group consisting of methanol and dimethyl ether (DME).

10. The method according to claim 7, wherein a ratio of a mass flow rate of the regenerated catalyst to a feed amount of the oxygen-containing compound is 0.3 to 1.0 ton of catalyst/ton of methanol.

11. The method according to claim 7, wherein process operating conditions of the reaction zone of the fluidized bed reactor are as follows: apparent gas linear velocity: 0.5 m/s to 7.0 m/s; reaction temperature: 350° C. to 550° C.; reaction pressure: 100 kPa to 500 kPa; and bed density: 100 kg/m$^3$ to 500 kg/m$^3$.

12. The method according to claim 7, wherein process operating conditions of the spent catalyst zone of the fluidized bed reactor are as follows: apparent gas linear velocity: 0.1 m/s to 1.0 m/s; reaction temperature: 350° C. to 550° C.; reaction pressure: 100 kPa to 500 kPa; and bed density: 200 kg/m$^3$ to 800 kg/m$^3$.

13. The method according to claim 7, wherein the first activation zone raw material comprises oxygen, air, and water vapor;
a mass fraction of the oxygen is 0 wt % to 10 wt %;
a mass fraction of the air is 0 wt % to 20 wt %; and
a mass fraction of the water vapor is 80 wt % to 100 wt %.

14. The method according to claim 7, wherein the second activation zone raw material is water vapor.

15. The method according to claim 7, wherein a coke content in the spent catalyst is 9 wt % to 13 wt %;
the spent catalyst comprises an SAPO-34 molecular sieve.

16. The method according to claim 7, wherein a coke content in the regenerated catalyst is 5 wt % to 11 wt %;
a quartile deviation of a coke content distribution in the regenerated catalyst is less than 1.0 wt %;
in the regenerated catalyst, coke species comprise polymethylbenzene and polymethylnaphthalene;
a total mass of the polymethylbenzene and the polymethylnaphthalene accounts for greater than or equal to 60 wt % of a total mass of coke;
a mass of coke species with a molecular weight greater than 184 accounts for less than or equal to 30 wt % of the total mass of coke; and
the total mass of coke refers to a total mass of coke species.

17. The method according to claim 7, wherein process operating conditions of the first activation zone of the fluidized bed regenerator are as follows: apparent gas linear velocity: 0.1 m/s to 0.5 m/s; temperature: 650° C. to 750° C.; pressure: 100 kPa to 500 kPa; and bed density: 400 kg/m$^3$ to 700 kg/m$^3$.

18. The method according to claim 7, wherein process operating conditions of the second activation zone of the fluidized bed regenerator are as follows: apparent gas linear velocity: 0.1 m/s to 0.5 m/s; temperature: 550° C. to 700° C.; pressure: 100 kPa to 500 kPa; and bed density: 400 kg/m$^3$ to 700 kg/m$^3$.

19. The fluidized bed regenerator according to claim 1, wherein m perforated plates are horizontally arranged in the second activation zone,
wherein 1≤m≤10;
the perforated plates have a porosity of 5% to 50%; and
second activation zone distributor is arranged at a bottom of the second activation zone.

20. The fluidized bed regenerator according to claim 1, wherein the fluidized bed regenerator comprises a regenerator gas collection chamber and a fluidized bed regenerator cooler;
the regenerator gas collection chamber is located at a top of the fluidized bed regenerator;
a top of the regenerator gas collection chamber is provided with a regenerator product gas delivery pipe;
the gas-solid separation zone is provided with a gas-solid separation unit;
the regenerator gas collection chamber is connected to an outlet of the gas-solid separation unit; and
the fluidized bed regenerator cooler is located in a lower part of the second activation zone.

* * * * *